United States Patent
Chang et al.

(10) Patent No.: US 10,955,380 B2
(45) Date of Patent: Mar. 23, 2021

(54) METHODS AND APPARATUS FOR A SHEAR-ENHANCED CNT-ASSEMBLY NANOSENSOR PLATFORM FOR ULTRA-SENSITIVE AND SELECTIVE PROTEIN DETECTION

(71) Applicant: University of Notre Dame du Lac, South Bend, IN (US)

(72) Inventors: Hsueh-Chia Chang, South Bend, IN (US); Diya Li, South Bend, IN (US); Satyajyoti Senapati, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 94 days.

(21) Appl. No.: 15/813,077

(22) Filed: Nov. 14, 2017

(65) Prior Publication Data
US 2018/0136163 A1 May 17, 2018

Related U.S. Application Data

(60) Provisional application No. 62/421,462, filed on Nov. 14, 2016, provisional application No. 62/484,758, filed on Apr. 12, 2017.

(51) Int. Cl.
  *G01N 27/414* (2006.01)
  *G01N 33/561* (2006.01)
  (Continued)

(52) U.S. Cl.
  CPC .......... *G01N 27/4146* (2013.01); *B82Y 5/00* (2013.01); *B82Y 15/00* (2013.01); *C12Q 1/003* (2013.01);
  (Continued)

(58) Field of Classification Search
  None
  See application file for complete search history.

(56) References Cited

U.S. PATENT DOCUMENTS

| | | | | |
|---|---|---|---|---|
| 6,060,023 A | * | 5/2000 | Maracas | G01N 27/3276 422/50 |
| 2004/0132220 A1 | * | 7/2004 | Fish | G01N 33/54313 436/525 |

(Continued)

FOREIGN PATENT DOCUMENTS

| | | |
|---|---|---|
| KR | 20160083167 A | 7/2016 |
| WO | 2006067276 A1 | 6/2006 |

OTHER PUBLICATIONS

Li et al, Biosensors and Bioelectronics, vol. 97, pp. 143-149, published online May 31, 2017.*

(Continued)

*Primary Examiner* — Robert T. Crow
(74) *Attorney, Agent, or Firm* — Greenberg Traurig, LLP (57) ABSTRACT

A nanoscale protein-sensing platform with a non-equilibrium on-off switch that employs dielectrophoretic and hydrodynamic shear forces to overcome these thermodynamic limitations with irreversible kinetics. The detection sensitivity is achieved with complete association of the antibody-antigen-antibody (Ab-Ag-Ab) complex by precisely and rapidly assembling carbon nanotubes (CNT) across two parallel electrodes via sequential DC electrophoresis and dielectrophoresis (DEP), and with single-CNT electron tunneling conductance. The high selectivity is achieved with a critical hydrodynamic shear rate between the activated dissociation shear rates of target and non-target linkers of the aligned CNTs.

12 Claims, 6 Drawing Sheets
Specification includes a Sequence Listing.

(51) Int. Cl.
| | |
|---|---|
| B82Y 5/00 | (2011.01) |
| B82Y 15/00 | (2011.01) |
| C12Q 1/00 | (2006.01) |
| G01N 27/12 | (2006.01) |
| G01N 33/541 | (2006.01) |
| G01N 33/543 | (2006.01) |

(52) U.S. Cl.
CPC ........... *C12Q 1/005* (2013.01); *G01N 27/127* (2013.01); *G01N 33/541* (2013.01); *G01N 33/5438* (2013.01); *G01N 33/54393* (2013.01); *G01N 33/561* (2013.01); *G01N 27/4145* (2013.01)

(56) References Cited

U.S. PATENT DOCUMENTS

| | | |
|---|---|---|
| 2004/0200734 A1 | 10/2004 | Co et al. |
| 2004/0235016 A1 | 11/2004 | Hamers et al. |
| 2006/0127942 A1 | 6/2006 | Straume et al. |
| 2009/0092989 A1 | 4/2009 | Chang et al. |
| 2010/0289509 A1 | 11/2010 | Chung et al. |
| 2011/0236984 A1* | 9/2011 | Sun ...................... C12Q 1/6869 436/94 |
| 2012/0190040 A1 | 7/2012 | Talebpour et al. |
| 2013/0068632 A1 | 3/2013 | Chang et al. |
| 2013/0306491 A1 | 11/2013 | Briman et al. |
| 2014/0349287 A1 | 11/2014 | Liu et al. |
| 2014/0357516 A1 | 12/2014 | Fletcher et al. |

OTHER PUBLICATIONS

Basuray S. et al., "Shear and AC Field Enhanced Carbon Nanotube Impedance Assay for Rapid, Sensitive, and Mismatch-Discriminating DNA Hybridization," ACS Nano [online], Jul. 31, 2009 [retrieved on Feb. 9, 2018], vol. 3, issue 7, retrieved from the Internet: <DOI: 10.1021/nn9004632>, pp. 1823-1830.
International Search Report and Written Opinion from International Application No. PCT/US17/61638, dated Mar. 7, 2018, nine (9) pages.
Allen, et al., "Detection of Antigen-Antibody Binding Events with the Atomic Force Microscope," Biochemistry, 36(24), 7457-7463, 1997.
Anderson, L., "Candidate-based proteomics in the search for biomarkers of cardiovascular disease," The Journal of physiology, 563(Pt I), 23-60, 2005.
Balasubramanian, et al., "Biosensors based on carbon nanotubes," Analytical and bioanalytical chemistry, 385(3), 452-468, 2006.
Basuray, et al., "Shear and AC Field Enhanced Carbon Nanotube: Impedance Assay for Rapid, Sensitive, and Mismatch-Discriminating DNA Hybridization," ACS Nano, 3(7), 1823-1830, 2009.
Berghoff, et al., "Co-overexpression of HER2/HER3 is a predictor of impaired survival in breast cancer patients," Breast (Edinburgh, Scotland), 23(5), 637-643, 2014.
Bruno, et al., "Targeting cytochrome P450 enzymes: a new approach in anti-cancer drug development," Bioorganic & medicinal chemistry, 15(15), 5047-5060, 2007.
Budman, et al., "Biomarkers for detection and surveillance of bladder cancer," Canadian Urological Association journal = Journal de l'Association des urologues du Canada, 2(3), 212-221, 2008.
Cheng, et al., "A rapid field-use assay for mismatch number and location of hybridized DNAs", Lab on a chip, 10(7), 828-831, 2010.
Chikkaveeraiah, et al., "Electrochemical Irnmunosensors for Detection of Cancer Protein Biomarkers," ACS Nano, 6(8), 6546-6561, 2012.
Findlay, et al., "Validation of immunoassays for bioanalysis: a pharmaceutical industry perspective," Journal of pharmaceutical and biomedical analysis, 21 (6), 1249-1273, 2000.
Gam, L.H., "Breast cancer and protein biomarkers," World journal of experimental medicine, 2(5), 86-91, 2012.
Glaser, R.W., "Antigen-antibody binding and mass transport by convection and diffusion to a surface: a two-dimensional computer model of binding and dissociation kinetics," Analytical biochemistry, 213(1), 152-161, 1993.
Gomes-Filho, et al., "A carbon nanotube-based electrochemical immunosensor for cardiac troponin T," Microchemical Journal, 109, 10-15, 2013.
Grieshaber, et al., "Electrochemical Biosensors—Sensor Principles and Architectures," Sensors (Basel, Switzerland), 8(3), 1400-1458, 2008.
Holmberg, et al., "The biotin-streptavidin interaction can be reversibly broken using water at elevated temperatures," Electrophoresis, 26(3), 501-510, 2005.
Hölzer, et al., "New simple correlation formula for the drag coefficient of non-spherical particles," Powder Technology, 184(3), 361-365, 2008.
Hortin, et al., "The dynamic range problem in the analysis of the plasma proteome," Journal of proteomics, 73(3), 629-636, 2010.
Hu, et al., "Modeling micropatterned antigen-antibody binding kinetics in a microfluidic chip," Biosensors and Bioelectronics, 22(7), 1403-1409, 2007.
Jia, et al., "Nano-ELISA for highly sensitive protein detection," Biosensors and Bioelectronics, 24(9), 2836-2841, 2009.
Kitano, H., "Systems biology: a brief overview," Science (New York, N.Y.), 295(5560), 1662-1664, 2002.
Kohno, et al., "Targeting the extracellular signal-regulated kinase pathway in cancer therapy," Biological & pharmaceutical bulletin, 34(12), 1781-1784, 2011.
Kokkinos, et al., "Electrochemical immunosensors: Critical survey of different architectures and transduction strategies," TrAC Trends in Analytical Chemistry, 79, 88-105, 2016.
Lilja, et al., "Prostate-specific antigen and prostate cancer: prediction, detection and monitoring," Nature reviews, Cancer 8(4), 268-278, 2008.
Maehashi, et al., "Label-Free Protein Biosensor Based on Aptamer-Modified Carbon Nanotube Field-Effect Transistors," Analytical Chemistry, 79(2), 782-787, 2007.
Pandiaraj, et al., "Designing label-free electrochemical immunosensors for cytochrome c using nanocomposites functionalized screen printed electrodes," Biosensors and Bioelectronics, 54, 115-121, 2014.
Pei, et al., "Sandwich-type immunosensors and immunoassays exploiting nanostructure labels: A review," Analytica Chimica Acta, 758, 1-18, 2013.
Privett, et al., "Electrochemical sensors," Anal Chem, 82(12), 4723-4741, 2010.
Rickert, et al., "A 'mixed' self-assembled monolayer for an impedimetric immunosensor," Biosensors and Bioelectronics, 11(8), 757-768, 1996.
Rusling, et al., "Measurement of biomarker proteins for point-of-care early detection and monitoring of cancer," The Analyst, 135(10), 2496-2511, 2010.
Srinivas, et al., "Trends in biomarker research for cancer detection," The Lancet, Oncology, 2(11), 698-704, 2001.
Stern, et al., "Importance of the Debye Screening Length on Nanowire Field Effect Transistor Sensors," Nano Letters, 7(11), 3405-3409, 2007.
Zhang, et al., "Glycoengineered Pichia produced anti-HER2 is comparable to trastuzumab in preclinical study," mAbs, 3(3), 289-298, 2011.
Zhang, et al., "Label-free electrochemical immunosensor based on enhanced signal amplification between Au@Pd and CoFe2O4/graphene nanohybrid," Scientific Reports, 6, 23391, 2016.
Zhou, et al., "CdSe nanowires with illumination-enhanced conductivity: Induced dipoles, dielectrophoretic assembly, and field-sensitive emission," Journal of Applied Physics, 101 (7), 073704, 2007.
Zhou, et al., "Bacteria capture, concentration and detection by alternating current dielectrophoresis and self-assembly of dispersed single-wall carbon nanotubes," Electrophoresis, 27(7), 1376-1385, 2006.

(56) References Cited

OTHER PUBLICATIONS

Zhu, et al. "Electrochemical Sensors and Biosensors Based on Nanomaterials and Nanostructures," Analytical Chemistry, 87(1), 230-249, 2015.

Extended European Search Report dated Oct. 27, 2020 for Application No. 17869405.5, 16 pages.

Basuray et al., "Shear and AC Field Enhanced Carbon Nanotube Impedance Assay for Rapid, Sensitive, and Mismath-Discriminating NDA Hybridization," ACS Nano, 3(7)1823-1830, 2009.

Chen et al., "SS-DNA-Decorated Single-Walled Carbon Nanotubes Integraed on CMOS Circuitry for High Sensitivity Gas Sensing," Transducers 2009: 2009 International Solid-State Sensors, Actuators and Microsystems Conference; Denver, Colorado, USA, Jun. 21-25, 2009, IEEE, Piscataway, NJ, USA, Jun. 21, 2009:1477-1480.

Wang et al., "Controlled assembly of zinc oxide nanowires using dielectrophoresis," Applied Physics Letters, A I P Publishing LLC, US, 90(10):103110-103110, 2007.

\* cited by examiner

METHODS AND APPARATUS FOR A SHEAR-ENHANCED CNT-ASSEMBLY NANOSENSOR PLATFORM FOR ULTRA-SENSITIVE AND SELECTIVE PROTEIN DETECTION

CROSS REFERENCE TO RELATED APPLICATION

This application is a non-provisional application claiming priority from U.S. Provisional Application Ser. No. 62/421,462, filed Nov. 14, 2016, entitled "A Shear-Enhanced CNT-DEP Nanosensor Platform for Ultra-Sensitive/Selective Protein Detection" and U.S. Provisional Application Ser. No. 62/484,758, filed Apr. 12, 2017, entitled "A Shear-Enhanced CNT-DEP Nanosensor Platform for Ultra-Sensitive/Selective Protein Detection" each of which is incorporated herein by reference in its entirety.

FIELD OF THE DISCLOSURE

The present description relates generally to protein detection via nanoscale biomarkers.

BACKGROUND OF RELATED ART

Conventional gold standard assay for protein detection is the enzyme-linked immunosorbent assay (ELISA). But the assay lacks the requisite detection sensitivity for many clinical samples due to high dissociation constant $K_D$ of most antibody-antigen pairs, rendering the antibody-antigen (Ab-Ag) complex thermodynamically unfavorable at target concentration lower than $K_D$. Since most antibodies have $K_D$ in the low µM to nM range, with a few high-affinity antibodies in the pM range, detections lower than pM are considered to be beyond reach by conventional devices. Furthermore, the detection dynamic range of conventional ELISA is often 2-3 orders of magnitude as a result of target saturation at equilibrium. This low dynamic range of assays is incompatible with in vivo physiological protein concentrations that vary over 4 orders of magnitude in serum, blood or urine. Lack of selectivity is another problem for the conventional ELISA assay that leads to false positives. For instance, false positive detection of bladder cancer urinary protein biomarker can be as high as 31%. False positives are caused by non-targets with similar $K_D$, which cannot be removed by conventional washing steps during the assay. Even if there is a significant difference in $K_D$ between targets and non-targets, the low-abundant targets cannot compete for the antibodies when the concentrations of the non-target proteins exceed that of the target by orders of magnitude. Therefore, development of a generic protein detection platform that has high sensitivity, selectivity and large dynamic range would then allow detection and quantification of arbitrary protein targets in untreated physiological samples by current commercial antibodies.

The nanoscale electrochemical immunoassay opens new horizons for highly sensitive yet simple and robust detection of biomarkers. In particular, CNT sensors provide a wide electrochemical window, fast electron transfer kinetics, and biocompatibility, which make them a good candidate for electrochemical molecular recognition. A CNT-FET label-free protein biosensors was reported by Maehashi et al. with a detection limit down to 250 pM. The detection is quantified by measuring source-drain current of CNT-FET as it changes with protein docking on the antibodies or aptamers functionalized surface. More recently, Gomes-Filho et al. overcome the detection limitation for an antibody-functionalized CNT ELISA sensor by using an enzymatic amplification technique with horseradish peroxidase (HRP) conjugated detection antibodies. The amperometric signals are thus amplified under optimum pH and buffer concentration with a detection limit of 0.033 ng/ml (~1 pM). Pandiaraj et al., on the other hand, doped the system with redox species Fe (III)/Fe (II), which decreases the charge-transfer resistance $R_{ct}$ to improve the sensitivity.

DETAILED DESCRIPTION

The following description of example methods and apparatus is not intended to limit the scope of the description to the precise form or forms detailed herein. Instead the following description is intended to be illustrative so that others may follow its teachings.

The device of this disclosure provides sensitive, selective, rapid and affordable detection of biomolecules, and particularly, proteins, has applications in early detection/diagnosis/screening and monitoring disease progressions. It allows detection and quantification of low-concentration proteins in heterogeneous media that are generally plagued by two distinct obstacles: lack of sensitivity due to high dissociation equilibrium constant $K_D$ and non-specificity due to an abundance of non-targets with similar $K_D$. Herein, a nanoscale protein-sensing platform with a non-equilibrium on-off switch employs dielectrophoretic and hydrodynamic shear forces to overcome these thermodynamic limitations with irreversible kinetics. The detection sensitivity is achieved in the disclosed example with complete association of the antibody-antigen-antibody (Ab-Ag-Ab) complex by precisely and rapidly assembling carbon nanotubes ("CNT") across two parallel electrodes via sequential DC electrophoresis and dielectrophoresis ("DEP"), and with single-CNT electron tunneling conductance. The high selectivity is achieved in the disclosed example with a critical hydrodynamic shear rate between the activated dissociation shear rates of target and non-target linkers of the aligned CNTs. Detection limits of 100 attomolar (aM) and 10 femtomolar (fM) in pure samples were reached for two ELISA assays with low and high dissociation constant: biotin/streptavidin (10 fM) and HER2/HER2 antibody (0.44±0.07 nM), respectively. For both models, irreversible capture and shearing allow tuning the dynamic range up to 5 decades by increasing the CNT numbers. Spiked serum sample high selectivity towards target HER2 proteins are demonstrated against non-target HER2 isoform of a similar $K_D$. The detection limit for HER2 in serum is lower than 100 fM.

Referring now to FIGS. 1A-D, an example nanosensor platform 10 of this disclosure is shown, specifically a schematic representation of the open-flow CNT on-off switch based biomolecule detection platform that employs two major non-equilibrium steps. The nanosensor platform 10 is built of a two lower electrodes, a first electrode 102A and a second electrode 102B, and a top electrode 102C all of which are connected to a current source 104. Polyclonal capture antibodies 106 are functionalized on the surface of the electrodes 102A, 102B. Over the electrodes 102A, 102B is a solution containing targets 108, non-targets 110, and carbon nanotubes 112, acting as conductive carriers, which are wrapped in DNA strands 114 are affixed to monoclonal detection antibodies 116.

Figure 1A:
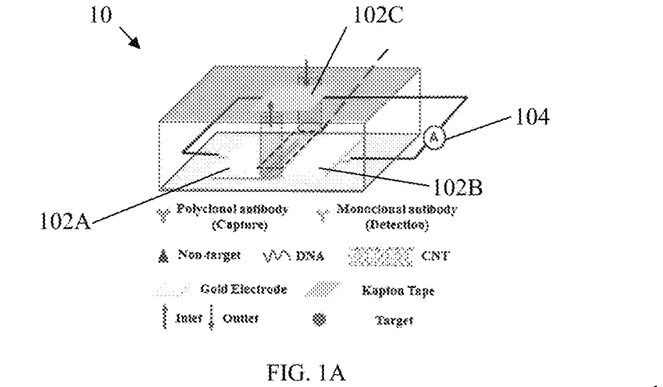
FIG. 1A is a schematic of a one-dimensional CNTs switch nanosensor platform for protein detection according to the teachings of the present disclosure.
Figure 1B:
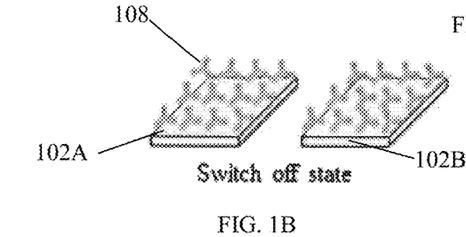
FIG. 1B shows the example nanosensor platform of FIG. 1A in its "off" or equilibrium state without any target material.

FIG. 1B shows the nanosensor platform 10 in its "off" state before any targets are added. The gold electrodes designed for the example nanosensor 10 in this study were patterned by photolithography. The electrodes could also be formed by chemical deposition or any other suitable method.

In the example nanosensor platform 10, the electrodes 102A, 102B, and 102C are arranged to apply electric fields to the microfluidic solution flowing across the platform 10. The first electrode 102A is positioned on a first surface of a chip comprising the support of the nanosensor platform. The second electrode 102B is positioned on a second surface displaced from the first surface at a distance and placing the second electrode 102B opposing the first electrode 102A in one direction. A top electrode 102C is positioned on a third surface above the first and second surfaces which places the top electrode 102C opposite both the first and second electrodes 102A, 102B in a direction orthogonal to the first direction. Prior to metal deposition, the glass slides were soaked in base piranha for 3 minutes and washed thoroughly with DI water. To fabricate 1 μm gap size electrodes, a pattern mask was fabricated from 300 mm double side Taflon insulate tape, and the mask was then taped onto the glass for 20 nm Cr and 175 nm gold e-beam deposition (Oerlikon Leybold 8-pocket electron-beam, dual thermal evaporation system). After the mask was removed, a 1 μm wide, and 550 μm long gap was created with a focused ion beam equipment. The chip was then soaked in Cr etchant for 4 seconds to remove any excess Cr in the gap. To fabricate 3 μm gap size electrodes, the chip was coated with 20 nm Cr and 175 nm gold under e-beam deposition. Then the chip was spin-coated with a layer of Shipley s1813 photoresist and sequentially exposed under a mask with 3 μm wide gap by a mask aligner (Karl Suss MJB-3 contact mask aligners). The chip was developed in AZ 917 MIF followed by a hard back at 90° C. for 60 seconds. The chip was dry etched by $Cl_2/BCl_3$ (ICP, 6 minutes, 200 W), and wet gold etched for 3 seconds. At last, the Cr layer was removed by Cr etchant, followed by sequential ethanol wash to remove excess photoresist layer.

The top electrode 102C was made by placing a 1 mm×15 mm aluminum foil on the center of a 20 mm×20 mm glass slide and sealed with Taflon insulate tape. A PDMS channel with a width of 800 μm and a length of 20 mm was then attached to the glass slide.

Referring again to FIG. 1B, a probe chosen to capture the target biomolecule by electrostatic attraction is placed on the electrode. In the example shown, this nanostructure is the polyclonal capture antibodies 106 which are functionalized on the electrode 102A, 102B. In one example of the disclosed nanosensor platform 10, an 11-mercaptoundonaic acid was dissolved in 95% of alcohol to make a 5 mM of thiol solution. After the pH was adjusted to 2 with HCl, electrode bearing chips with 1 μm wide gap were incubated in the solution with $N_2$ gas purging for 5 minutes to remove air in the solution. The electrode bearing chips were incubated and then transferred to a 30 ml of 95% alcohol solution to remove access thiol layers by ultrasonicating at 30% power for 6 minutes. After carefully drying the chip with nitrogen gun, and a 2 mm diameter wide silicon isolator was attached to the chip on top of the separated electrodes. 20 μl of 100 mM of EDC was added to react with the COOH group on the thiol layer for 25 min. The chip was rinsed with 20 μl of MES solution 3 times to remove any non-reacted EDC. To functionalize biotins onto gold electrodes as for the example nanosensor platform 10 discussed below with respect to FIGS. 2A-C below, 20 μl of 50 mM of biotin in MES solution was added and incubated for four hours. To functionalize capture (polyclonal) HER2 antibody onto gold electrodes as for the example discussed below with respect to FIGS. 3A-B below, 20 μl of 0.09 mg/ml polyclonal HER2 antibody in 1× PBS was added and incubated for four hours.

Figure 1C:
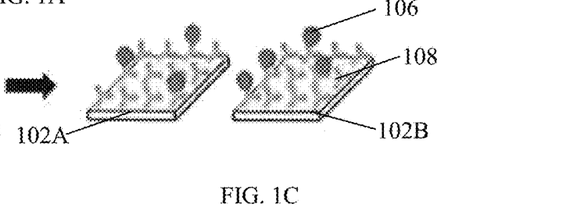
FIG. 1C shows the example nanosensor platform of FIG. 1A with a target material added.
Figure 1D:
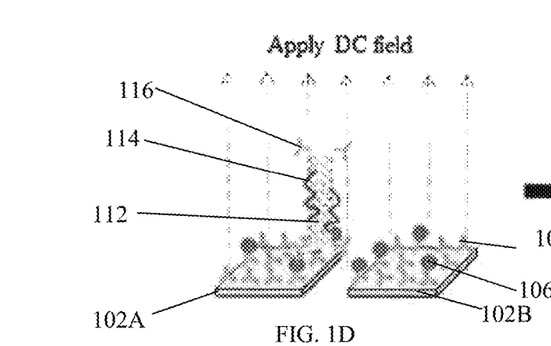
FIG. 1D shows the example nanosensor platform of FIG. 1A exhibiting the alignment of the example detection nanotubes under a DC field.

Referring to FIGS. 1C and 1D, which shows the target (FIG. 1C) and the conductive carriers in the solutions. In the example shown, the carriers are carbon nanotubes 112 acting as the conductive carrier. The nanotubes 112, with monoclonal capture antibodies 116 attached being introduced in a solution. The monoclonal capture antibodies 116 are adapted to strongly bind to the target biomolecule via electrostatics. The monoclonal capture antibodies 116 are configured to cooperate with the polyclonal capture antibodies 106 to both simultaneously bind to the same target biomolecule and thereby connecting the nanotube 112 to the surface of the electrodes 102A, 102B. In this way, the large conductive carrier can be used to detect the presence of the target and if present allow current flow.

In one example nanosensor platform 10, the solution is created with 4 mg of 1 to 3 μm COOH-SWCNTs were added into 6 ml of DI water, and the solution was ultra-sonicated with is pulse and is rest for 2 minutes under 40% power (10 Watts) using Qsonica sonicators. Then the solution was centrifuged for 90 minutes at 18334 g. The upper 1 ml of CNTs solution was collected as the stock solution for CNT functionalization. As the CNTs in this example, are of 1-3 µm length, for the example sensing study, chips bearing the nanosensor platform 10 are fabricated with 1 µm gap in order to have 100% of CNTs capable of bridging.

As shown in FIG. 1D, the bridge DNA-wrapped and detection (monoclonal) antibody-functionalized carbon nanotubes 110 is introduced with the size long enough to connect across the two electrodes 102A, 102B. Single strand DNA tested in this example was a sequence of 5' TGG TTC TCT CCG AAA TAG CTT TAG GG (Seq. No. 1) of molecular weight is 8898.8 g/mol, However a wide variety of DNA targets are considered, such that can be attached to the monoclonal antibodies attached to the CNT. The carbon nanotubes 112 are wrapped in DNA strands 114 in order to disperse the CNT in the solution, such as 1×PBS, efficiently. To accomplish this aided dispersal in the example nanotube 110 tested in this disclosure, 40 µl of dispersed CNTs from the 1ml stock CNT solution was mixed with 40 µl of 1 mM ssDNA solution. The samples of nanotubes 110 were then placed for ultrasonication with Qsonica sonicators at 20% power with 1 s pulse and 1 s rest for 5 min. The DNA non-specifically binds/wraps around the side-walls of the CNTs, thus increasing the negative charge on CNTs and making them easily dispersed in 1×PBS.

Monoclonal detection antibodies 116 are affixed to the surface of the carbon nanotube 110 to bind to the target bio-molecule, such as biotin or HER2 in the examples discussed below. In the example nanosensor platform 10 tested in this disclosure, this accomplished by 10 µl of EDC in MES solution being added to the solution to react with the COOH groups on the CNTs, and the solution was ultrasonicated with Qsonica sonicators at 20% power with 1 s pulse and 1 s rest for 5 min. To functionalize biotins onto CNTs as for the example nanosensor platform 10 discussed below with respect to FIGS. 2A-C below, 10 µl of 50 mM of biotin in MES solution was then added to link COOH groups on CNT for 2 hrs and the solution was gently mixed with a rotator. At last, the solution was transferred to a dialysis kit to remove any non-bounded biotin and EDC for 6.5 hours. The dialysis solution was collected and used as biotin functionalized CNTs stock solution. To functionalize detection (monoclonal) HER2 antibody onto CNTs as for the example nanosensor platform 10 discussed below with respect to FIGS. 3A-C below, 10 µl of 0.05 mg/ml of monoclonal HER2 antibody in 1×PBS solution was added to bind to the COOH groups for 2 hrs. During the two hours, the solution was gently mixed with a rotator. At last, the example solution was centrifuged at a speed of 13.3 g for 5 minutes, and the supernatant was collected and used as HER2 antibody functionalized CNTs stock solution.

Referring again to FIG. 1D, carbon nanotubes 112 can be aligned by electric forces of the electrodes 102A, 102B. This is achieved by an irreversible assembly phenomenon, driven first by DC electrophoresis that rapidly attracts and aligns the CNTs vertically on top of the electrodes as the CNTs are attracted to the polyclonal antibodies on the surface of the Ag electrode. Since the DC field has a relatively long range with the high electric fields applied here, a majority of the negatively charged CNTs can be attracted to the electrodes within one minute. Their electrostatic repulsion sustains equal spacing between the vertically aligned CNTs along the DC field lines.

In the example nanosensor platform 10, the alignment process uses DC and AC to induce DC and AC DEP protocols on bare Gold electrodes. In the tested example nanosensor platform, the dispersed CNTs were diluted 10,000 times with DI water, and 5 µl of the dispersed CNTs solution was loaded into the channel to be aligned under different deposition protocol on 3 µm wide gold electrodes, and the deposition time was 5 minutes for all three protocols. 100V DC voltage was applied, and a AC voltage with a $V_{pp}$ value of 5 V at 5 MHz was applied.

Figure 1E:
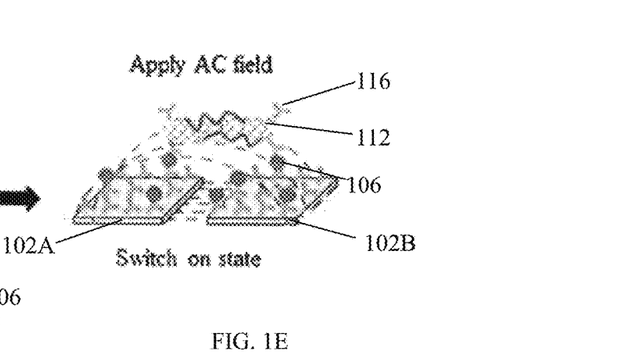
FIG. 1E shows the example nanosensor platform of FIG. 1A exhibiting the alignment of the example detection nanotubes under an AC field.

Referring to FIG. 1E, AC DEP is activated to quickly align the CNTs horizontally as shown in, resulting in bridging of the two electrodes and formation of the Ab-Ag-Ab CNT complexes. The bridged CNTs transform the system into a switch-"on" mode and conduct current by CNT electron tunneling.

Figure 1F:
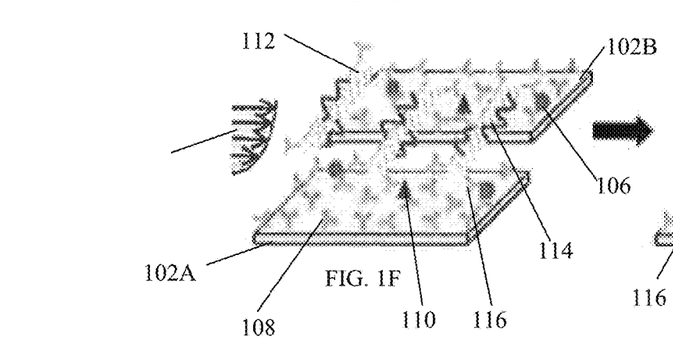
FIG. 1F shows the example nanosensor platform of FIG. 1A undergoing a process of hydrodynamic shear to boost selectivity.

The step shown in FIG. 1F improves the selectivity of detection by hydrodynamic shearing. Because of the large hydrodynamic drag imposed by a cross-flow on cylindrical CNTs with high aspect ratio, selectively the non-target or no-target bound CNTs are removed under a critical flow shear rate. The remaining aligned target-antibody bound CNTs will produce current signals that will be correlated with the target (CNT) number as shown in FIG. 1G.

In an example of the nanosensor platform 10, the optimization of flow rate of the hydrodynamic shearing flow when using Biotin-Streptavidin as an antibody-antigen pair was conducted. After the top electrode was attached to the chip with four clamps secured at four corners, 5 µl of the biotin functionalized CNTs was loaded into the channel. 5 min of 100V DC voltage was first applied vertically by connecting the top electrodes and two bottom electrodes, and then quickly switched to a horizontal AC voltage connection the bottom electrodes 102A, 102B with a $V_{pp}$ value of 5 V at 5 MHz for 15 minutes. After the biotin functionalized CNTs were aligned by both directional current flows, a syringe with 1× PBS solution was connected to the channel to shear off non-specifically bounded no-target CNTs. Different shear rate was tested to find the optimal rate of 0.5 ml/min. Then, CNTs with varied concentration was deposited to test the removal percentage under the optimum shear rate. The percentage of shear was based on the current change before and after shear, and all current measurements were conducted at 1V with Gamry Potentiostat 600.

Figure 1G:
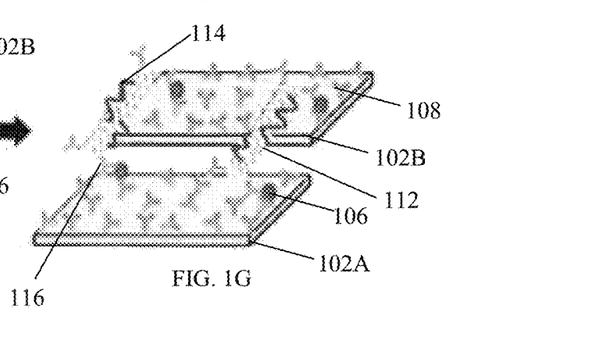
FIG. 1G shows the example nanosensor platform of FIG. 1A with only bound target molecules.

Referring now to FIG. 1G, the remain nanotubes serve for the detection of the. It is contemplated that the DC and AC dielectrophoresis field strengths, target incubation time, shearing buffer efficacy, CNT concentrations, and electrode area would be varied to improve the performance of the nanosensor platform 10.

Figure 2A:
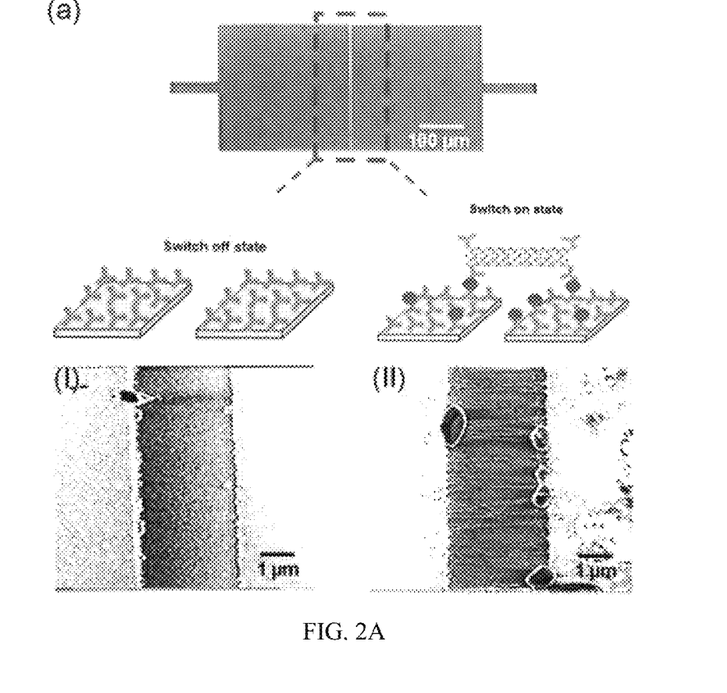
FIG. 2A shows a comparison of an example nanosensor platform according to the teachings of this disclosure with insets to show the off or without targets (a) and on with targets (b) states shown in SEM images.
Figure 2B:
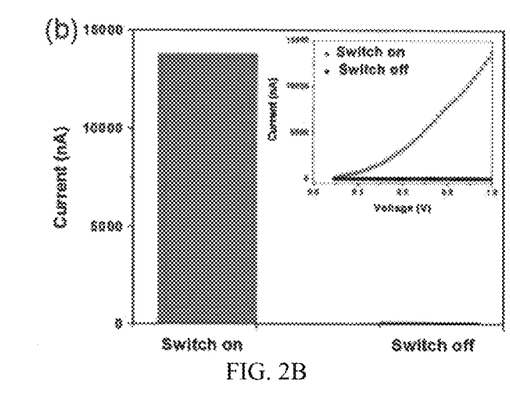
FIG. 2B is a graph of the current (in nanoampears) of the off and on states of the example nanosensor platform.

FIG. 2A illustrates one example schematics of switch on and off states used in these studies, where CNTs act as current reporters. Preliminary studies validating the methods discussed above were conducted on parallel clean gold electrodes, shown in FIG. 2A, with 3 µm to test CNTs alignment using the sequential DC and AC DEP protocol. The aligned CNTs at "switch on" state produce a current signal that is 5 orders of magnitude more than that of the "switch off" state at 1V as demonstrated in the chart shown in FIG. 2B. Such a large current differences demonstrate highly sensitive and effective conductance between CNTs and electrodes at the "switch on" state. The large current difference contributes to a very low and stable baseline current at the "switch off" state, because the current is exclusively carried by CNTs bridging, without measurable parasitic currents from electrochemical reactions at the electrodes. As a result, the baseline current is negligibly small with the absence of CNTs and remains inert to other conditions such as different pH, buffer ionic strength or the types of buffer solutions. SEM images of CNTs alignments under different deposition concentrations show that most of CNTs align in parallel bridging across the electrodes without aggregation, and any small aggregations near the edge of the electrodes are due to the evaporation of the solvents before imaging. Since the length of CNTs is between 1-3 μm, there are CNTs with shorter lengths that cannot bridge the electrodes.

Figure 2C:
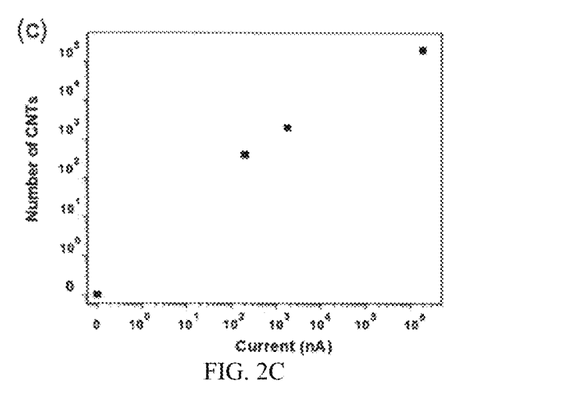
FIG. 2C indicates a correlation between current signal with respective to CNT numbers when DC/AC deposition technique is used.

However, bridged CNTs had such good alignments, and the number of CNTs bridged was easily estimated and plotted against the corresponding current illustrated in FIG. 2C. FIG. 2C shows a linear relationship between the current and the number of CNTs aligned, with a correlation coefficient of 0.99 from the linear regression. Extrapolating our data to a single CNT, the theoretical detection limit can hence go down to aM to fM if there are, on the average, 2 to 2000 antigens on a single carbon nanotube with 10 μl of sample volume, including ones on the electrodes that have not formed complexes with the CNT. The dynamic range also goes up to 6 orders of magnitude, and can be further expanded by decreasing gap size, and increasing the polyclonal antibody density on gold electrode and the number of CNTs deposited. The low detection limit and large dynamic range of this platform would then allow us to detect a wide range of protein biomarkers with different concentrations.

Figure 3A:
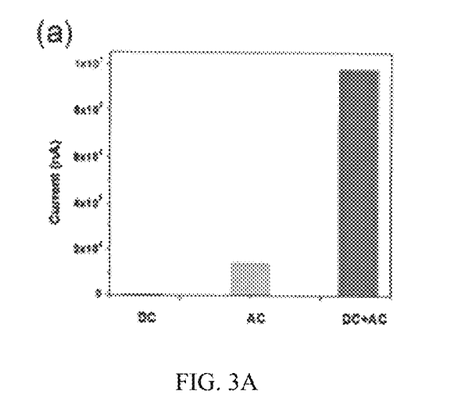
FIG. 3A depicts the currents changes due to three different deposition methods, DC, AC, and DC+AC.
Figure 3B:
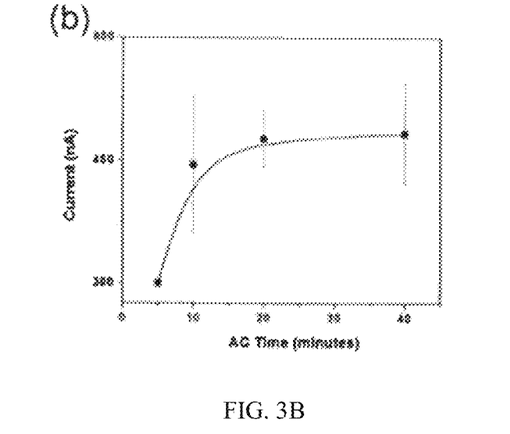
FIG. 3B is a graph showing currents were measured after AC assisted deposition.
Figure 3C:
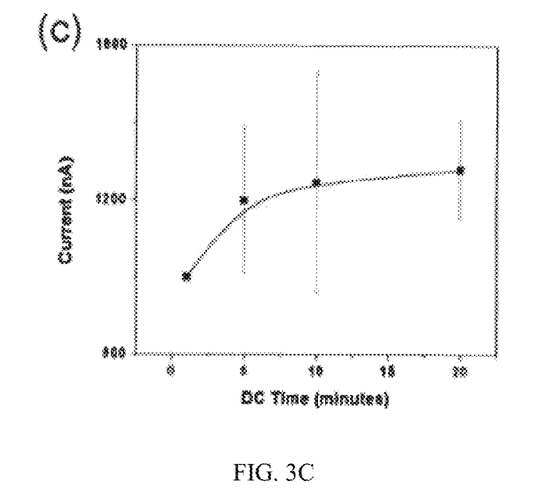
FIG. 3C is a graph showing currents were measured after DC assisted deposition

Referring now to FIGS. 3A-3C, DC, AC and combined DC/AC DEP depositions were tested to optimize DC deposition and AC alignment for assembling CNTs into individual parallel and regimented bridges across the electrode pairs. Under the same deposition time and same CNT concentration, the results of measured current from different methods are presented in FIG. 3A. The combined DC and AC DEP deposition shows the highest current, which is about five times more than that of AC deposition alone. Since the process of AC DEP exists in a short-range field, any CNTs that are outside the AC DEP range will not feel the electric field gradient and will not be aligned between the electrodes. DC electrophoresis is long-range and can attract all the CNTs to the parallel gold electrodes but it alone cannot bridge the CNTs across the electrodes, which explains why there is no current change for DC deposition. So it is only when sequential DC and AC DEP deposition are used that the maximum number of CNTs can be attracted to and assembled on the gold electrodes.

Referring now to FIG. 3B, studies were conducted to find the optimal DC and AC deposition times. FIG. 3B depicts that under the same DC time, the amount of CNTs aligned increases with AC DEP time. However, the current gradually reaches a plateau, indicating an optimum AC time of 15 minutes. On the other hand, under a same AC time of 5 minutes, DC time is optimized in FIG. 3C. The current reaches a plateau after 5 minutes of DC application. Together, the optimal time for combined DC and AC DEP deposition time is about 20 minutes, which is far less than diffusion limited detection antibody incubation for conventional ELISA assay. Moreover, the disclosed combined DC and AC DEP deposition technique forces essentially all the detection antibodies-functionalized CNTs to bind with the targets on the gold electrodes, far beyond the thermodynamic equilibrium values.

Figure 4A:
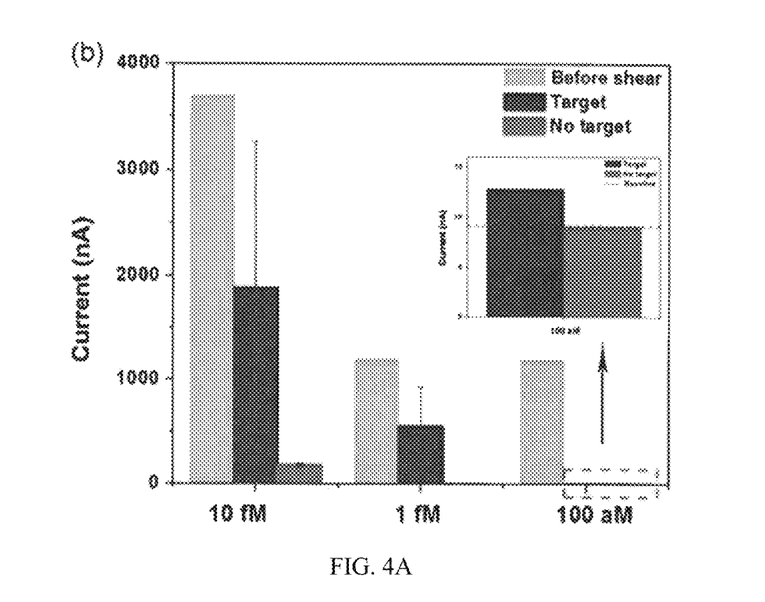
FIG. 4A depicts selectivity results of target and non-target incubation after irreversible shearing.
Figure 4B:
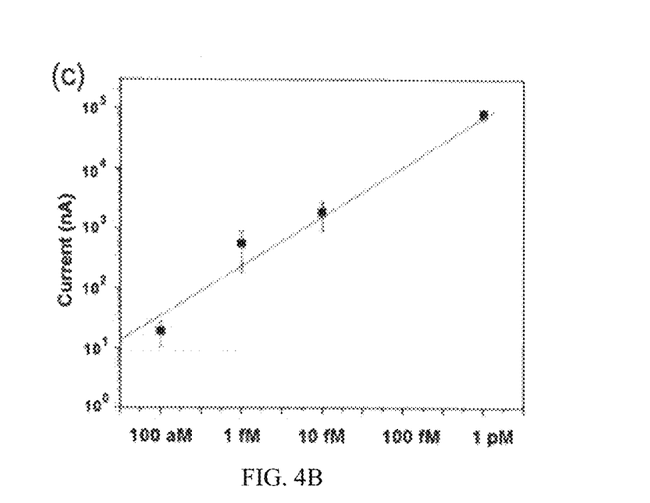
FIG. 4B indicates the calibration curve of the streptavidin concentration, where the detection limit is 100 aM, and the dynamic range is 5 orders of magnitude.

In order to examine the feasibility of the disclosed platform according to the teachings of this disclosure and confirm its sensitivity and selectivity, a streptavidin and biotin pair was used as an example system shown in FIGS. 4A-4B. Biotin and streptavidin pairs in the example have very strong binding affinity as compared with antigen-antibody pairs in real clinical sample. The dissociation constant for biotin and streptavidin is 10 fM, and bonds are stable through a wide range of pH and temperature. Biotin is used as both capture antibody and detection antibody, and pure streptavidin were used as target.

In this example, the biotin solution was stored in a freezer at 4° C. until ready for use, and streptavidin was stored at −20° C. The samples were slowly dissolved at 0° C. before use. In order to functionalize the biotin, 0.1 M of MES (pH 5.5) was prepared by dissolving 10.861 g MES sodium salt in 500 ml of DI water, and the pH is adjusted with 0.5M of NaOH. 100 mM of EDC solution was made by dissolving 19 mg EDC in 1 ml of MES solution, and 50 mM of biotin solution was prepared with 19 mg biotin in 1 ml of MES solution. Different concentration of Streptavidin was dissolved in 1× PBS. To demonstrate that hydrodynamic shear is selective towards target streptavidin, the experiments were designed on chips with and without streptavidin.

In the example nanosensor platform 10, detection of the target, in this case, Streptavidin, was accomplished using 20 μl of streptavidin solution was added onto the biotin functionalized chips and incubated at room temperature. After incubation, the chip was rinsed 3 times with 1× PBS to remove non-bounded streptavidin. 10 μl of biotin antibody functionalized CNTs solution was diluted 10,000, 100,000, and 1,000,000 times with 0.1× PBS. Then the top electrode was attached to the chip, and 5 μl of the diluted biotin antibody functionalized CNTs was loaded into the channel to align and bridge the electrodes under DC and AC dielectrophoresis assisted disposition. For streptavidin, CNT solutions with 1,000,000 times of dilution was deposited to detect 100 aM and 1 fM. CNTs with 10,000 times of dilution were used for 10 fM and 1 pM. CNTs with 10,000 and 1,000 times of dilution were used for 10 pM and 100 pM, respectively. After shearing at 0.5 ml/min with 1× PBS for 20 minutes, the current was measured at 1V using Gamry.

Referring now to FIG. 4A, the current results of the example biotin-streptavidin validations are shown. After biotin functionalized CNTs are aligned, the disclosed flow step (described above with regard to FIG. 1F) will irreversibly remove any CNTs that have not bound to any streptavidin. FIG. 4B has confirmed that under the same CNTs deposition, a flow rate at 0.5 ml/min can remove more than 99% of the CNTs when no streptavidin is incubated. When streptavidin is incubated, the targets are able to hold CNTs on the electrodes with strong binding forces to withstand the drag force exerted on the CNTs under shear. Moreover, FIG. 4B indicates that the higher concentration of streptavidin incubates, the more target antibody CNT complexes form to produce higher current. Thus, experimental results support that flow shearing can selectively remove no-target bound CNTs. Selectivity is directly related to the flow shear rate, and a high shear rate can remove both no-target and target bound CNTs, so it is important to optimize shear rate in order to achieve high selectivity.

At the same time, the number of CNTs needs to be selected such that the antibody probes on the CNTs are higher than the number of targets to avoid target saturation. In fact, by optimizing the number of CNTs with respect to target concentrations, the dynamic range can be linearly extended without target saturation. So with the optimal number of CNTs, a calibration curve is shown in FIG. 4C for the 100 aM to 1 pM range of a pure streptavidin sample. The graph reveals a linear regime from 100 aM to 1 pM with a correlation coefficient of 0.97 from linear regression, and the detection limit of 100 aM is 2 orders of magnitude lower than the dissociation constant for biotin and streptavidin pair. At 100 aM concentration, there are about 10 CNTs bridging across the electrodes based on the linear correlation from FIG. 2C, and the numbers of targets on each of CNTs are around 20 assuming all streptavidin bind. Such a low detection limit is a result of sensitive CNTs electron tunneling at "switch on" state, and the low baseline current and noise level at "switch off" state, where there is no CNTs or electrochemical reactions to contribute to current. The linear calibration curve indicates a dynamic range that could be 5 orders of magnitude more if higher streptavidin concentrations are used. In all, the example use of biotin and streptavidin detection has shown that the nanosensor platform is sensitive and selective toward targets with CNTs concentrations optimized for target concentrations.

Figure 5A:
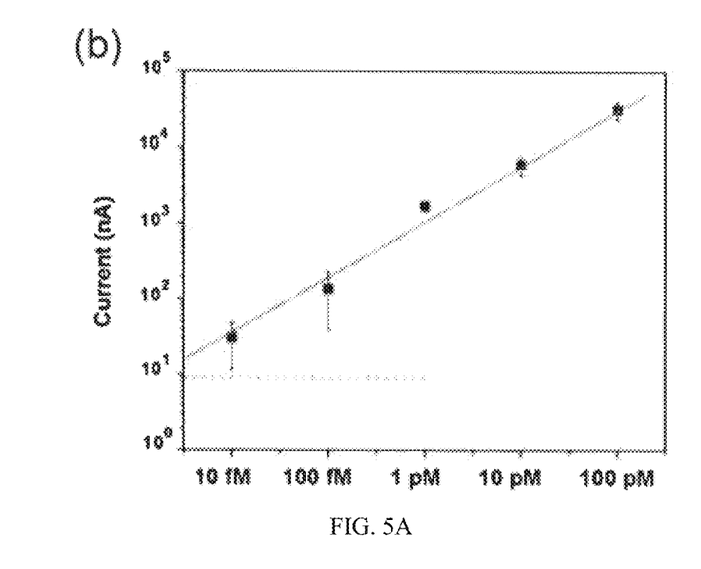
FIG. 5A indicates the calibration curve of different HER2 concentrations, where the detection limit is 10 fM, and the dynamic range is 5 orders of magnitude.
Figure 5B:
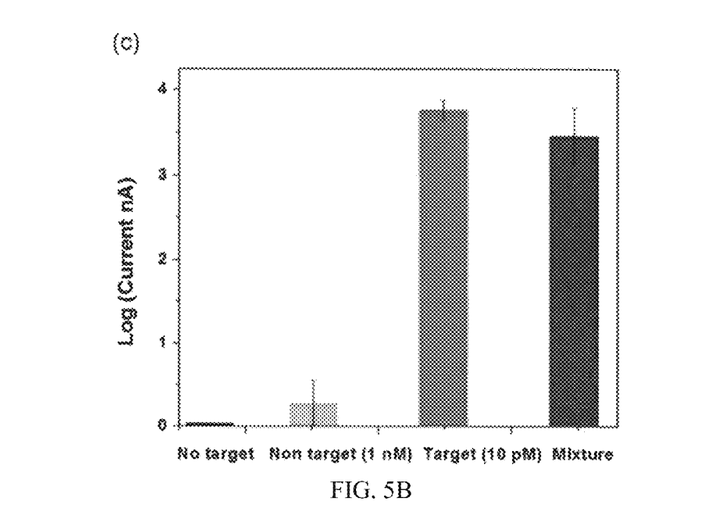
FIG. 5B depicts selectivity results of target and no target incubation with an HER2 target.

Referring to FIGS. 5A-5B, a breast cancer biomarker HER2 and HER2 antibody pair is selected in order to evaluate the sensitivity and selectivity of the platform against real protein and antibody pairs which usually have higher dissociation constants when used with the nanosensor platform of this disclosure. HER2 is an important biomarker for breast cancer, and its status is routinely assessed when breast cancer is diagnosed. An overexpression of HER2 is a significant predictor of reduced survival rate and shorter time to relapse. The $K_D$ of HER2 and its antibody is around 0.44±0.07 nM, so it is more challenging to detect HER2 at lower concentrations. Pure HER2 samples were tested first to find the detection limit and dynamic range for this low binding affinity pair. In this example, the HER2 sample was stored in a freezer at −20° C. until ready for use. The sample was slowly dissolved at 0° C. before use. The negative control HER2 was dissolved in 1× PBS to a concentration of 1 nM while the target HER2 was dissolved in 1× PBS to concentration of 10 pM.

Iii the example nanosensor platform 10, detection of the target, in this case, HER2, was accomplished using 20 μl of HER2 solution was added onto the biotin functionalized chips and incubated at room temperature. After incubation, the chip was rinsed 3 times with 1× PBS to remove non-bounded streptavidin. 10 μl of capture HER2 antibody functionalized CNTs solution was diluted 10,000, 100,000, and 1,000,000 times with 0.1× PBS. Then the top electrode was attached to the chip, and 5 μl of the diluted capture HER2 antibody functionalized CNTs was loaded into the channel to align and bridge the electrodes under DC and AC dielectrophoresis assisted disposition. For HER2, 10 fM to 1 pM of targets were detected with CNT solutions with 1,000,000 times of dilution. CNTs with 10,000 and 1,000 times of dilution were used for 10 pM and 100 pM, respectively. After shearing at 0.5 ml/min with 1× PBS for 20 minutes, the current was measured at 1V using Gamry.

The calibration curve was developed in FIG. 5A from 10 fM to 100 pM. The graph reveals a linear regime for all measured target concentrations with a correlation coefficient of 0.989. As illustrated, the detection limit is 10 fM, which is higher than that of the biotin and streptavidin model. Since the dissociation constant of HER2 is 10,000 times higher than that of biotin and streptavidin, only higher concentrations of incubated targets can form efficient Ab-Ag complexes to hold the CNTs against the drag force during flow shearing. 10 fM of detection limit is 4 orders of magnitude lower than its $K_D$ value, which is a result of DC and AC DEP CNT deposition technique that facilitates the formation of Ab-Ag complex at much lower target concentration. This study shown in FIGS. 5A-5B clearly demonstrates that the example nanosensor platform is highly sensitive with a dynamic range up to 5 orders of magnitude.

A stringent selectivity test was done with a HER2 isoform as the non-target negative control as shown in FIG. 5A. This HER2 isoform is a partial recombinant protein that binds to the detection antibody with the same binding affinity as the target HER2. However, it binds to the capture antibody with less affinity. This study illustrates the nanosensor platform can avoid a "false positive" results by using such a similar target molecule.

For comparison of breast cancer biomarker HER2, this negative control and isoform mixture was introduced. To the solution, 20 μl of HER2 solution, 20 μl of, and 20 μl of a mixture of 10 pM HER2 and 1 nM of negative control non-target HER2 were added into the capture antibody functionalized chips respectively to incubate at room temperature. After incubation, the chips were rinsed with 1×PBS 3 times. Then the top electrodes were attached, and 5 μl of the 10,000 times diluted detection HER2 antibody functionalized CNTs with the same concentration were loaded into the channel to align and bridge the electrodes under DC and AC dielectrophoresis assisted disposition for the same time. After shearing at 0.5 ml/min with 1×PBS for 20 minutes, the currents were measured at 1V using Gamry, and the differences were compared between the two chips.

FIG. 5B illustrates that the flow shearing removes more than 95% of the HER2 isoform non-targets bound CNTs. But HER2 bound CNTs complex are able to stand the shearing step with a current that is 1000 times higher than that of the non-target HER2. The concentration of the non-target HER2 isoform is 1 nM, which is 100 times higher than target concentration of 10 pM, indicating an effective shear-enhance discrimination of non-targets by a factor of several orders of magnitude. To further validate the sensor's selectivity performance, a mixture of 10 pM target and 1 nM non-target sample was tested. Despite the presence of 100 times more non-targets, the current value is still 3 orders of magnitude higher than that of the non-target isoform sample shown in FIG. 5B. The current of mixture sample is slightly less than that of pure target samples due to site competitions between targets and non-targets. In all, this example nanosensor platform adapted to HER2 detection further confirms that the flow shearing is highly selective towards targets despite the presence of non-targets with high concentration.

Figure 6:
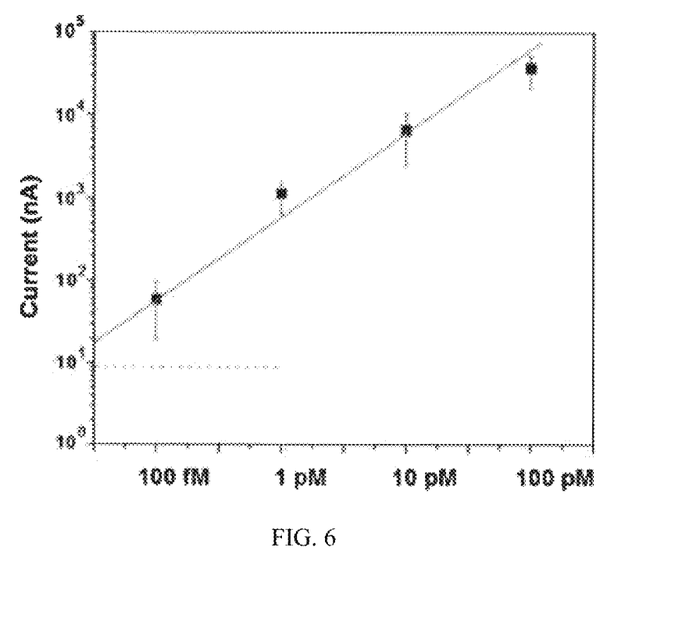
FIG. 6 shows a calibration curve of the HER2 spiked in the human serum, where the detection limit is 100 fM, and the dynamic range is 4 orders of magnitude.

Referring to FIG. 6, further validations of the performance of an example nanosensor platform with a heterogeneous sample were preformed to provide calibration information. In this study, four different concentrations of HER2 targets were selected and spiked them into undiluted human serum, since human serum has a high abundance of non-target proteins that could potentially compete with targets for complex association with antibodies. Measurements in this example were conducted with only human serum to create a baseline with different CNTs concentrations to eliminate the effect of pre-existing HER2 in serum. A calibration curve was developed and presented in FIG. 6. The graph reveals a linear regime for all measured target concentrations with a correlation coefficient of 0.98. At a 100 fM concentration, the detected current is well above the noise line of the baseline, indicating a detection limit lower than 100 fM. Nevertheless, 100 fM of detection is already 3 orders of magnitude lower than the dissociation constant of HER2 and its antibody pair. This makes the detection sensitivity one order of magnitude lower than that of pure sample. However, a detection of 100 fM is still better than the limit of any commercially available HER2 ELISA kit. At the same time, the detection dynamic range is 4 orders of magnitude, and this value can continue to increase for higher concentration target detection based on the linearity of the calibration curve.

In the example, the detection of breast cancer biomarker HER2 in undiluted serum sample was tested in a 20 µl of HER2 serum solution with known concentration was added into the capture antibody functionalized chips to incubate at room temperature. After incubation, the chip with the example nanosensor platform 10 was rinsed with 1× PBS 3 times to remove non-bounded HER2. Then the top electrode was attached to the nanosensor platform 10, and 5 µl of the diluted detection HER2 antibody functionalized CNTs was loaded into the channel to align and bridge the electrodes under DC and AC dielectrophoresis assisted disposition. 100 fM to 1 pM of HER2 were detected with CNT solutions with 1,000,000 times of dilution. CNTs with 10,000 and 1,000 times of dilution were used for 10 pM and 100 pM, respectively. After shearing at 0.5 ml/min with 1×PBS for 20 minutes, the current was measured at 1V using Gamry.

In all, the sensitive, selective and quantifiable CNT-ELISA nanosensor platform for protein detection according to the teachings of the present disclosure, which assembles individual antibody functionalized CNTs to bridge across the electrodes to bind with targets. The CNTs serve both as a transporter and a reporter for the target-linker. The DC electrophoresis and AC dielectrophoresis assisted deposition and assembly helps to achieve rapid CNTs deposition while facilitates target and antibody binding by bringing them closer. The use of 1× PBS hydrodynamic shearing produces enhanced drag force on the CNTs that irreversibly removes the CNTs bound to no-targets or non-targets, thus also elevating the selectivity beyond the thermodynamic limits. As a result, the example nanosensor platform discussed above detects low dissociation constant model and high dissociation constant model down to 100 aM and 10 fM respectively, within a 20 µl sample volume. At the same time, the assay is highly selective against non-targets with similar binding affinity, even when such non-targets outnumber the targets by three orders of magnitude. The test of the example device using human serum results further confirm that the assay remains sensitive and selective in heterogeneous mixtures with a detection limit lower than 100 fM for the complex with 0.44±0.07 nM $K_D$. Therefore, the example nanosensor platform potentially improved the performance of conventional ELISA assay by sub-fM detection limit (2 orders improvement) and 4-decade dynamic range (1 or 2 orders improvement) for HER2 serum sample by scaling the initial CNTs concentrations with the target concentrations.

Therefore, the example nanosensor platform disclosed herein significantly enhances both the thermodynamic sensitivity and selectivity of the ELISA complex with non-equilibrium and irreversible phenomena related to CNTs.

The CNTs are used as capturing, reporting and selectivity enhancement agents in conjunction with a precise but rapid assembly technique. The high aspect ratio of the CNT endows them with large induced dipoles, large dielectrophoretic mobility and large hydrodynamic drag. After targets are introduced to bind with polyclonal capture antibodies on the parallel gold electrodes that are 1 µm separated, a solution containing the monoclonal detection antibodies functionalized CNTs with wrapped DNAs are driven by DC electrophoresis and AC dielectrophoresis (DEP) to assemble across the electrode pair and form antigen-antibody-antigen (Ab-Ag-Ab) ELISA complex. The rapid and irreversible DC and AC DEP trapping not only captures more targets than is allowed by molecular association at equilibrium, but also significantly reduces the overall assay time compared to diffusion-limited assays. Prior work has proven that the high AC field at assembled CNTs across two parallel electrodes can rapidly isolate bacteria and long DNAs in a flowing solution by dielectrophoresis. Next, a cross-flow passes across the assembled CNTs to irreversibly shear off non-target-CNT complexes, thus enhancing the selectivity of the platform. Since the hydrodynamic drag force of CNTs is inversely proportional to the nature log of CNT's aspect ratio, the force is 2 orders of magnitude higher than that of a normal wash without CNTs. The force can be precisely tuned with shear rate to achieve the optimal selectivity for a Ab-Ag pair, as the CNTs are perfectly aligned in the assembly. Only target-CNTs complexes remain after shear, and the number of detectable targets is governed by the CNT number that can be easily tuned to produce a large dynamic range. As a result, we have developed the disclosed robust CNT protein nanosensor platform that is simple and rapid, with sub-aM sensitivity and high specificity over a 5-decade dynamic range.

However, it is known that the test example CNT-FET charge sensor can only detect charged proteins within one Debye length from the surface of the CNT and is hence sensitive to the sample ionic strength. Even though enzymatic/redox-reporter amplifies current signal, those electroactive species activities are strongly influenced by the medium pH, which may affect the conformations of target proteins and thus limits the detection sensitivity in the tested example. Moreover, long-term presence of the redox probes or enzyme influences the activity of the immobilized proteins. The stability of enzyme functionality and thermodynamic affinity of the enzyme-conjugated antibodies can potentially compromise the high CNT sensitivity.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents.

We claim:

1. A method of detecting a presence of a plurality of biomolecules, the method comprising:
    continuously flowing a sample solution comprising target biomolecules through a nanosensor platform having at least a first surface with a first electrode and a second surface displaced from the first surface at a distance and having a second electrode opposing the first electrode;
    providing a first probe on the first electrode, wherein the first probe is formed by functionalizing a first binding molecule complementary to the target biomolecules;
    flowing a solution containing the target biomolecules and a conductive carrier including a second probe, wherein the second probe is formed by functionalizing a second binding molecule complementary to the target biomolecules;
    hybridizing at least one of the target biomolecules with the first probe on the surface of the first electrode and the second probe on the conductive carrier forming at least one hybridized probe;
    applying a first voltage across the first electrode and a third electrode, wherein the first voltage is configured such that a direct current field is applied across the first electrode and the third electrode, and further wherein the direct current field arranges the conductive carrier in a first orientation;
    hydrodynamically shearing at least one of a non-target biomolecule from the first electrode or the second electrode;
    after applying the first voltage, applying a second voltage across the first electrode and the second electrode, wherein the second voltage is configured such that an alternating current field is applied across the first electrode and the second electrode, and further wherein the alternating current field arranges the conductive carrier in a second orientation; and
    evaluating the at least one hybridized probe by measuring an electrical current between the first and second electrodes to determine a presence of the target biomolecules.

2. The method of detecting the presence of the plurality of biomolecules of claim 1 wherein the third electrode is positioned orthogonally to the first and second electrodes and the alternating current field is orthogonal to the direct current field.

3. The method of detecting the presence of the plurality of biomolecules of claim 1 wherein the direct current field is applied before the alternating current field to boost the hybridization of the first and second probes.

4. The method of detecting the presence of the plurality of biomolecules of claim 1 wherein the conductive carrier in the second alignment bridges the distance between the first and second electrodes.

5. The method of detecting the presence of the plurality of biomolecules of claim 1, further comprising evaluating the electrical current between the first and second electrodes to determine a quantity of the target biomolecules.

6. The method of detecting the presence of the plurality of biomolecules of claim 1 wherein the conductive carrier is a carbon nanotube.

7. The method of detecting the presence of the plurality of biomolecules of claim 6 wherein the carbon nanotube is increased in negative charge by the addition of a charge carrier.

8. The method of detecting the presence of the plurality of biomolecules of claim 7 wherein the carbon nanotube is bound to a DNA.

9. The method of detecting the presence of the plurality of biomolecules of claim 1, further comprising applying the second voltage between the first and second electrodes over a period of time.

10. The method of detecting the presence of the plurality of biomolecules of claim 9 wherein electrophoresis brings the target biomolecules into contact with the first probe and dielectrophoresis bridges the carbon nanotube between the first and second electrodes.

11. The method of detecting the presence of the plurality of biomolecules of claim 1 wherein the first voltage comprises one hundred volts (100 V) direct current voltage and is applied for approximately five (5) minutes.

12. The method of detecting the presence of the plurality of biomolecules of claim 1 wherein the second voltage comprises an alternating current voltage with a $V_{pp}$ value of five volts (5 V) at five megahertz (5 MHz) and is applied for approximately fifteen (15) minutes.

* * * * *

SEQUENCE LISTING

<160> NUMBER OF SEQ ID NOS: 1

<210> SEQ ID NO 1
<211> LENGTH: 26
<212> TYPE: DNA
<213> ORGANISM: Artificial Sequence
<220> FEATURE:

```
<223> OTHER INFORMATION: Synthetic

<400> SEQUENCE: 1
tggttctctc cgaaatagct ttaggg                                                  26
```